United States Patent [19]
Hamilton

[11] Patent Number: 5,467,776
[45] Date of Patent: Nov. 21, 1995

[54] AIR SAMPLING DEVICE AND METHOD FOR SAMPLING EXHALED AIR

[75] Inventor: Steven D. Hamilton, Greenfield, Wis.

[73] Assignee: The Brewer Company, Menomonee Falls, Wis.

[21] Appl. No.: 98,537

[22] Filed: Jul. 28, 1993

[51] Int. Cl.[6] ................................................. A61B 5/097
[52] U.S. Cl. ......................................................... 128/730
[58] Field of Search ................................... 128/716, 719, 128/727, 728, 730, 725, 202.12

[56] References Cited

U.S. PATENT DOCUMENTS

| | | | |
|---|---|---|---|
| 3,817,108 | 6/1974 | Principe et al. | 128/730 |
| 4,544,273 | 12/1970 | McConnoughey | 128/719 |
| 4,671,298 | 6/1987 | Babb et al. | 128/719 |
| 4,852,583 | 8/1989 | Walker | 128/716 |
| 5,042,500 | 8/1991 | Norlien et al. | 128/719 |
| 5,042,501 | 8/1991 | Kenny et al. | 128/719 |
| 5,140,993 | 8/1992 | Opekun, Jr. et al. | 128/730 |

*Primary Examiner*—Lee S. Cohen
*Assistant Examiner*—Brian M. Green
*Attorney, Agent, or Firm*—Wheeler & Kromholz

[57] ABSTRACT

An air sampling device for obtaining a sample of air from a person's lungs. The air sampling device is comprised of a blow tube connected to a waste air collection bag, and an air capture assembly connected to the blow tube by a needle assembly, for directing a portion of the air from the blow tube into the air sample capture assembly. The air sample capture assembly including a test tube containing a vacuum and having a rubber stopper that separates the vacuum contained within the test tube from the needle assembly connected to the blow tube. The rubber stopper is capable of being pierced by a needle of the needle assembly at a predetermined time. Additionally, the invention includes a method of using the air sampling device for obtaining a sample of air from a person's lungs. The method comprising: a first step in which the person blows a predetermined volume into the blow tube and a second step in which the rubber stopper separating the needle assembly from the inside of the test tube containing the vacuum is pierced after the predetermined volume is expelled by the person into the blow tube and a portion of the air blown by the person is captured in the test tube and the needle is subsequently withdrawn and the rubber stopper reseals itself or is sealed.

9 Claims, 2 Drawing Sheets

AIR SAMPLING DEVICE AND METHOD FOR SAMPLING EXHALED AIR

BACKGROUND OF THE INVENTION

The present invention relates generally to the field of sampling air that is exhaled from a patient's lungs and specifically to the field of obtaining a sample of alveolar air containing $CO_2$ generated from an isotope of carbon; either a stable isotope such as Carbon 13 or a radioisotope such as Carbon 14. Alveolar air is air from the alveoli of the lungs of a person.

Air from the lungs of a person can be used for many different types of testing that would otherwise require the person to undergo an invasive type of therapy. For example, air from the alveoli of a person's lungs can be analyzed for the noninvasive diagnosis of *helicobacter pylori* (a stomach infection related to a high incidence of ulcers). Crucial to any such testing is the ability to get an accurate sample containing a sufficient volume of air representative of true alveolar air, which is necessary for the specific testing required. The present invention by means of a unique and simple design and method achieves this goal.

The applicant knows of no prior art that either teaches or shows the present invention. For example, U.S. Pat. No. 4,947,861 (Hamilton), an invention developed by the present inventor's father, discloses a structure and method for the noninvasive diagnosis of gastritis and duodenitis that uses a method for sampling the air from the alveoli of a person's lungs by use of an impermeable collecting bag but does not disclose nor suggest either the method or the simple and straightforward structure of the present invention. Likewise other sampling devices of the prior art use techniques that require either that the person or some other person obtain the sample by use of a pump or syringe that was activated manually.

Those methods of sampling can prove to be cumbersome and since different persons or persons may draw the sample in variously different ways such methods do not always produce consistent levels of suction or the reproducible timing required to draw a valid sample. Accordingly, such methods introduce an additional variable that can potentially affect the outcome of a particular test. The present invention by means of its unique and simple design and method eliminates this variable to produce a structure and method that may obtain a reliable sample of the air from the lungs of a person in a safe, accurate, and noninvasive manner.

SUMMARY OF THE INVENTION

The present invention is an air sampling device for obtaining a sample of air from a person's lungs. The air sampling device is comprised of a blowing means, typically a simple tube connected to a waste air collection bag, for allowing the person to blow air therethrough, wherein the unwanted air is received in the waste air collection bag, and an air capture assembly connected to the blowing means by a conduit means, typically a needle assembly, for directing a portion of the air from the blowing means into the air sample capture assembly. The air sample capture assembly including a vacuum chamber, a test tube or other such device suitable for holding an air sample, containing a vacuum and having a wall that separates the vacuum contained within the vacuum chamber from the conduit means connected to the blowing means. The wall is usually a rubber stopper that is capable of being pierced by the needle that is the conduit means so that the wall is capable of being opened and closed to the conduit means at a predetermined time.

Additionally, the invention includes a method of using the air sampling device for obtaining a sample of air from a person's lungs. The method comprising: a first step in which the person blows into the blowing means to expel a predetermined volume of air into the waste bag and a second step in which the wall separating the conduit means from the vacuum chamber containing a vacuum is opened at the appropriate time the person is blowing into the blowing means so that a desired portion of the air blown by the person is captured in the vacuum chamber and the wall is closed or sealed.

DETAILED DESCRIPTION

Figure 1:
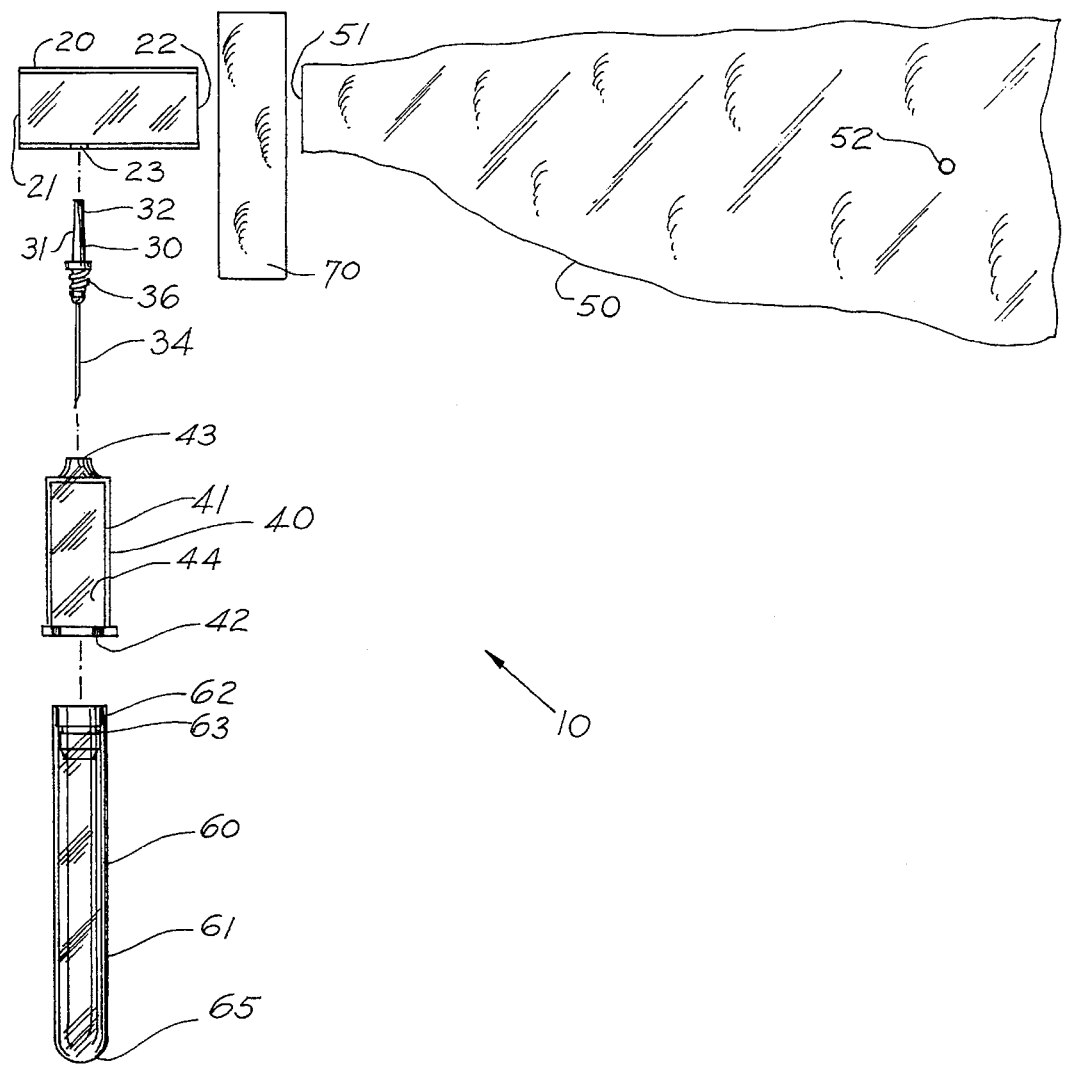
FIG. 1 is an exploded side view of the present invention showing the component parts of the invention.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Referring to FIGS. 1–4 the present invention 10 may be seen to be structurally composed of a blow tube 20, a needle assembly 30, a needle assembly holder 40, a waste air bag 50, and a vacuum sample tube assembly 60.

Figure 2:
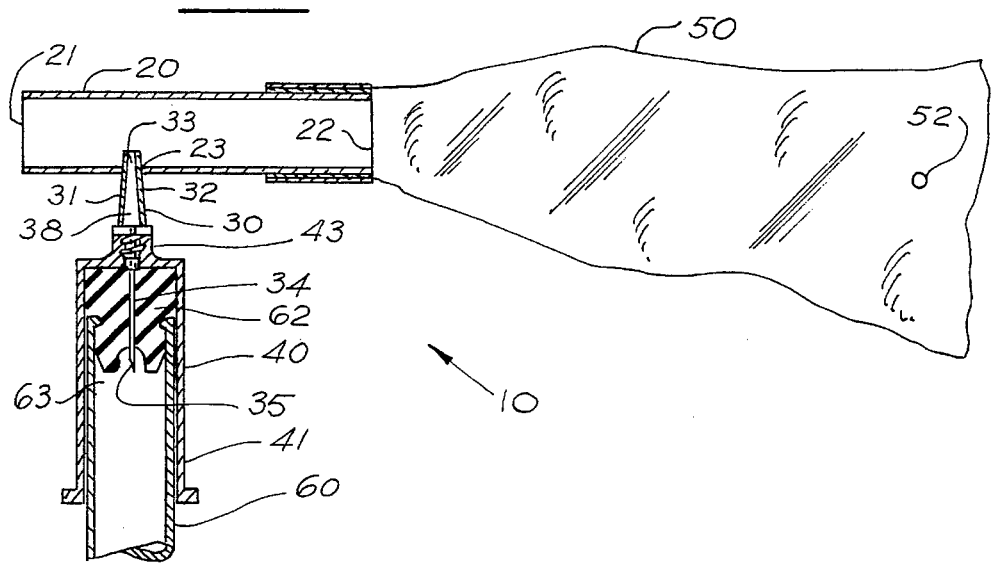
FIG. 2 is a cutaway side view of the present invention, showing the invention assembled for sampling.

Referring specifically to FIGS. 1 and 2 the structure of the invention 10 may be seen to be interrelated as follows: the blow tube 20 has open ends 21 and 22 and a sampling port or opening 23. The waste bag 50 has an open end 51 that is taped in place by a piece of tape 70 when the open end 51 is placed over the open end 22 of the blow tube 20. The waste bag 50 further including a small vent hole 52 which permits the patient to continue to exhale at a reduced rate after the waste bag 50 is brought to full inflation. The needle assembly 30 has a threaded sampling tube 31, having threads 36, that has an end 32, having an opening 33, that is dimensioned to tightly fit into the sampling port 23 of the blow tube 20, so that the end 32 extends into the blow tube 20. A hollow needle 34, having and open end 35, is fixedly connected to the sampling tube 31 so that a conduit channel 36, extending from opening 33 of the sampling tube to open end 35 of the needle 34, is created.

Still referring to FIGS. 1 and 2 it may be seen that the needle assembly holder 40 comprises a tube 41 having a hollow interior 44, a large open end 42 designed to receive the vacuum sample tube 60 into the hollow interior 44, and a smaller threaded opening 43 designed to be screwed onto the threads 36 so that the needle 34 can extend into the hollow interior 44.

Figure 4:
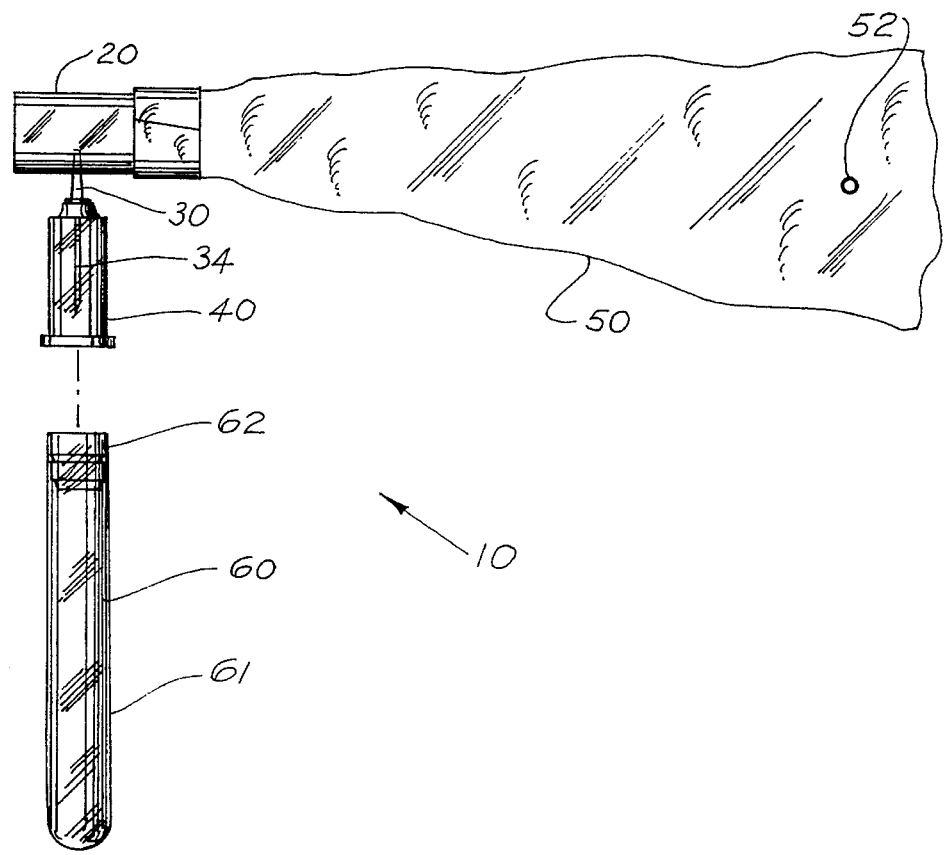
FIG. 4 is a partially exploded side elevational view of the present invention.

Still referring to FIG. 2, but also to FIGS. 1 and 4, the vacuum sample tube 60 may be seen to be an evacuated test tube 61, with an open end 63 and a closed end 65, having a stopper 62 made of rubber or some other material sufficiently resilient.

Figure 3:
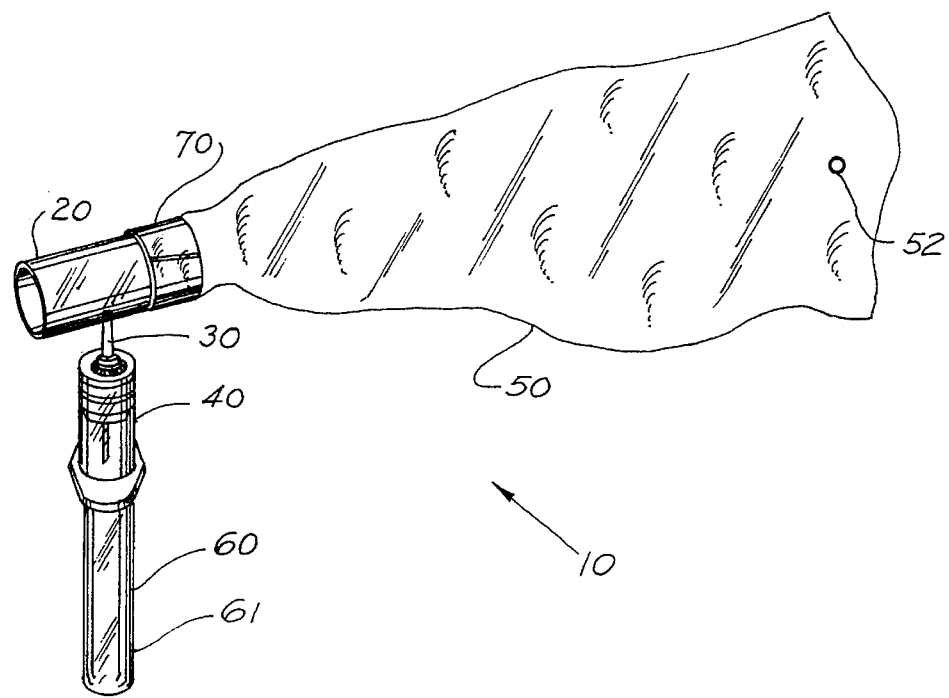
FIG. 3 is a perspective view of the present invention.

Referring now to all the Figures the invention 10 may be seen to function as follows: The person from whose lungs a sample of alveolar air is desired blows through the open or blowing end 21 of the blow tube 20 so that the waste bag 50 (attached to the exit end 22 of the blow tube 20), which is made from a supple and air-tight material, is brought to full inflation by the exhalation of the person. This causes the removal from the lungs of what is referred to as "dead space air", i.e. the air that issues from the oral cavity, the nose, the trachea, and the bronchi of the person during the initial phase of exhalation of the person. The filling of the waste bag 50 to capacity provides a visual signal to the person that the dead space or undesired air has been exhaled and that the final portion of air to be exhaled is the desired alveolar air located deep within the lungs. The small aperture or vent 52 in the waste bag 50 allows the patient to continue to breathe out (i.e. exhale) at a reduced rate while the next step, shown in FIG. 3, is initiated.

The ability of the patient to exhale at a reduced rate, due to the ventilation of the bag 50 by the aperture 52, is advantageous in that it allows greater control over the sampling process. However, the invention could be practiced, albeit less effectively, without the use of the waste bag 50.

At that time the person or a technician working with the person can insert the evacuated test tube 61 into the hollow 44 of the needle assembly holder 40 so that the rubber stopper 62 is pierced by the needle 34 and the predetermined vacuum contained within the test tube 61 supplies a sufficient predetermined level of suction necessary to draw a sufficient sample of the desired air from the lungs of the person. The test tube 61 may then be immediately withdrawn from the hollow 44 of the needle assembly holder 40 and the resilient rubber stopper 62 will reseal itself to protect and contain the sample drawn from contamination.

Alternatively, an additional cover or seal may be placed over the rubber stopper 62 to ensure that the test tube 61 is properly sealed.

Accordingly, a sample of air from the lungs of a person may be obtained quickly and easily by the means of the structure and process of the present invention. Further, it should be noted that the test tube 61 could be preloaded with desiccant or a chemical indicator for a variety of tests in addition to those tests specifically disclosed herein.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An air sampling device for obtaining a sample of alveolar air from a person's lungs, the air sampling device comprising:

a blowing means for allowing the person to blow air therethrough;

an air sample capture assembly connected to the blowing means by a conduit means for directing a portion of the air from the blowing means into the air sample capture assembly, the conduit means being directly connected to the blowing means;

the air sample capture assembly including a vacuum chamber containing a vacuum and having a permeable rubber membrane capable of being punctured and resealed at a predetermined time separating the vacuum from the conduit means connected to said blowing means.

2. The air sampling device of claim 2 in which the blowing means has an opening connected to a waste bag means for capturing undesired air exhaled by the person exhaling into the blowing means.

3. The air sample device of claim 2 in which the waste bag means is a waste bag.

4. The air sample device of claim 1 in which the blowing means is a tube having a blowing end, an exit end, and a sample opening.

5. An air sampling device for obtaining a sample of air from a person's lungs, the air sampling device comprising:

a blowing means for allowing the person to blow air therethrough;

the blowing means having an opening connected to a waste bag for capturing undesired air exhaled by the person exhaling into the blowing means;

the waste bag having a ventilation means for allowing the person to exhale at a reduced rate through the blowing means;

an air sample capture assembly connected to the blowing means by a conduit means for directing a portion of the air from the blowing means into the air sample capture assembly;

the air sample capture assembly including a vacuum chamber containing a vacuum and having a wall separating the vacuum from the conduit means connected to said blowing means;

the wall being capable of being opened and closed to said conduit means at a predetermined time.

6. The air sampling device of claim 5 in which the ventilation means is an aperture in the waste bag.

7. An air sampling device for obtaining a sample of air from a person's lungs, the air sampling device comprising:

a blowing means for allowing the person to blow air therethrough;

an air sample capture assembly connected to the blowing means by a conduit means for directing a portion of the air from the blowing means into the air sample capture assembly;

the air sample capture assembly including an evacuated test tube containing a vacuum and having a rubber stopper separating the vacuum from the conduit means connected to said blowing means;

the rubber stepper capable of being opened and dosed to said conduit means at a predetermined time.

8. A method of using an air sampling device for obtaining a sample of air from a person's lungs, the air sampling device including a blowing means for allowing the person to blow therethrough; an air sample capture assembly connected to the blowing means by a needle assembly having a needle and connected to the blowing means at an opening for directing a portion of the air from the blowing means into the air sample capture assembly; the air sample capture assembly including an evacuated test tube containing a vacuum and having a rubber stopper separating the evacuated test tube from the needle assembly connected to said blowing means; the rubber stopper capable of being opened and closed to said needle assembly at a predetermined time, the method comprising:

a first step in which the person blows a predetermined volume of air through the blowing means;

a second step in which after the predetermined volume of air has been blown through the blowing means the needle is used to pierce the rubber stopper of the test tube and a sample of alveolar air from the person's lungs is sucked into the test tube by the vacuum of the test tube.

9. A method of using an air sampling device for obtaining a sample of air from a person's lungs, the air sampling device including a blowing means for allowing the person to blow air therethrough; art air sample capture assembly connected to the blowing means by a conduit means for directing a portion of the air from the blowing means into the air sample capture assembly; the blowing means having an opening connected to a waste bag for capturing undesired air exhaled by the person exhaling into the blowing means; the waste bag having a ventilation means for allowing the person to exhale at a reduced rate through the blowing means; the air sample capture assembly including a vacuum chamber containing a vacuum and having a permeable rubber membrane capable of being punctured and resealed at a predetermined time separating the vacuum from the conduit means connected to said blowing means, the method comprising:

a first step in which the person blows a predetermined volume of air through the blowing means filling the waste bag with the predetermined volume of air and continues to blow through the blowing means into the waste bag at the reduced rate;

a second step in which the permeable rubber membrane separating the conduit means from the vacuum chamber containing the vacuum is punctured after the person has blown the predetermined volume of air through the blowing means and a portion of the air blown by the person is captured in the vacuum chamber and the permeable rubber membrane is resealed.

* * * * *

UNITED STATES PATENT AND TRADEMARK OFFICE
CERTIFICATE OF CORRECTION

PATENT NO. : 5,467,776

DATED : November 21, 1995

INVENTOR(S) : Steven D. Hamilton

It is certified that error appears in the above-indentified patent and that said Letters Patent is hereby corrected as shown below:

In the Claims:
  Please amend the claims as follows:

2. The air sampling device of claim 1 in which the blowing means has an opening connected to a waste bag means for capturing undesired air exhaled by the person exhaling into the blowing means.

9. A method of using an air sampling device for obtaining a sample of air from a person's lungs, the air sampling device including a blowing means for allowing the person to blow air therethrough; an air sample capture assembly connected to the blowing means by a conduit means for directing a portion of the air from the blowing means into the air sample capture assembly; the blowing means having an opening connected to a waste bag for capturing undesired air exhaled by the person exhaling into the blowing means; the waste bag having a ventilation means for allowing the person to exhale at a reduced rate through the blowing means; the air sample capture assembly including a vacuum chamber containing a vacuum and having a permeable rubber membrane capable of being punctured and resealed at a predetermined time separating the vacuum from the conduit means connected to said blowing means, the method comprising:

UNITED STATES PATENT AND TRADEMARK OFFICE
CERTIFICATE OF CORRECTION

PATENT NO. : 5,467,776
DATED : November 21, 1995
INVENTOR(S) : Steven D. Hamilton It is certified that error appears in the above-indentified patent and that said Letters Patent is hereby corrected as shown below:

a first step in which the person blows a predetermined volume of air through the blowing means filling the waste bag with the predetermined volume of air and continues to blow through the blowing means into the waste bag at the reduced rate;

a second step in which the permeable rubber membrane separating the conduit means from the vacuum chamber containing the vacuum is punctured after the person has blown the predetermined volume of air through the blowing means and a portion of the air blown by the person is captured in the vacuum chamber and the permeable rubber membrane is resealed.

Signed and Sealed this

Twenty-third Day of November, 1999

Attest:

Q. TODD DICKINSON

*Attesting Officer*   *Acting Commissioner of Patents and Trademarks*